(12) United States Patent
Kidooka

(10) Patent No.: US 6,953,430 B2
(45) Date of Patent: Oct. 11, 2005

(54) PINCERLIKE INSTRUMENT FOR ENDOSCOPE

(75) Inventor: Satoshi Kidooka, Saitama (JP)

(73) Assignee: PENTAX Corporation, Tokyo (JP)

(*) Notice: Subject to any disclaimer, the term of this patent is extended or adjusted under 35 U.S.C. 154(b) by 0 days.

(21) Appl. No.: 10/797,125

(22) Filed: Mar. 11, 2004

(65) Prior Publication Data
US 2004/0186348 A1 Sep. 23, 2004

(30) Foreign Application Priority Data
Mar. 18, 2003 (JP) .................................... P2003-072865

(51) Int. Cl.[7] ................................................. A61B 1/00
(52) U.S. Cl. ........................ 600/104; 606/46; 606/51; 606/52; 600/153; 600/156
(58) Field of Search ..................... 600/104, 153, 600/156; 606/32, 46, 51, 52, 205–210

(56) References Cited

U.S. PATENT DOCUMENTS

| 5,330,471 | A | * | 7/1994 | Eggers | 606/48 |
| 5,810,876 | A | * | 9/1998 | Kelleher | 606/205 |
| 6,066,102 | A | * | 5/2000 | Townsend et al. | 600/564 |
| 6,129,683 | A | * | 10/2000 | Sutton et al. | 600/564 |
| 2001/0021859 | A1 | * | 9/2001 | Kawai et al. | 606/205 |
| 2001/0025149 | A1 | * | 9/2001 | Kobayashi et al. | 600/564 |
| 2003/0043264 | A1 | | 3/2003 | Furuya | |
| 2003/0191464 | A1 | | 10/2003 | Kidooka | |
| 2003/0216733 | A1 | * | 11/2003 | McClurken et al. | 606/51 |

FOREIGN PATENT DOCUMENTS

| JP | 10-165359 | 6/1998 |
| JP | 11-047135 | 2/1999 |
| JP | 4-146741 | 5/1999 |

OTHER PUBLICATIONS

English Language Abstract of JP 11–047135.

* cited by examiner

Primary Examiner—Beverly M. Flanagan
Assistant Examiner—Matthew Kasztejna
(74) Attorney, Agent, or Firm—Greenblum & Bernstein, P.L.C.

(57) ABSTRACT

A pincerlike instrument for an endoscope, comprising a flexible sheath, a pair of limbs, and a water supply channel. The pair of limbs, being provided at the fore-end of the flexible sheath, opens and closes as a pincers by remote operations from the base-end of the flexible sheath. The water supply channel is formed inside the flexible sheath for ejecting water from the fore-end of the flexible sheath by supplying the water from the base-end of the flexible sheath. A water ejection opening for the water supply channel is disposed at the base portion of the pair of limbs between the two limbs with the water ejection opening facing forward.

8 Claims, 5 Drawing Sheets

PINCERLIKE INSTRUMENT FOR ENDOSCOPE

BACKGROUND OF THE INVENTION

1. Field of the Invention

The present invention relates to pincerlike instruments for an endoscope, such as forceps.

2. Description of the Related Art

Biopsy forceps, holding forceps, hemostasis forceps, scissors forceps, and so on, are well known as a pincerlike instruments for an endoscope. The pincerlike instruments for an endoscope are devices having a pair of limbs, including blades, opposite each other at the distal end of a flexible sheath. The pair of limbs is remotely operated from the base end of the flexible sheath so that the limbs are opened or closed at the distal end.

SUMMARY OF THE INVENTION

An object of the present invention is to provide a pincerlike instrument for an endoscope, that can be used to carry out treatment of an affected part which is hemorrhaging, immediately after washing the blood from the affected part.

According to the present invention, a pincerlike instrument for an endoscope is provided that comprises a flexible sheath, a pair of limbs, and a water supply channel.

The pair of limbs is provided at the fore-end of the flexible sheath and is opened and closed like a pincers by remote operations from the base-end of the flexible sheath. The water supply channel is formed inside the flexible sheath for ejecting water from the fore-end of the flexible sheath by supplying the water from the base-end of the flexible sheath. A water ejection opening of the water supply channel is disposed at the base portion of the pair of limbs, between the two limbs with the water ejection opening facing forward.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
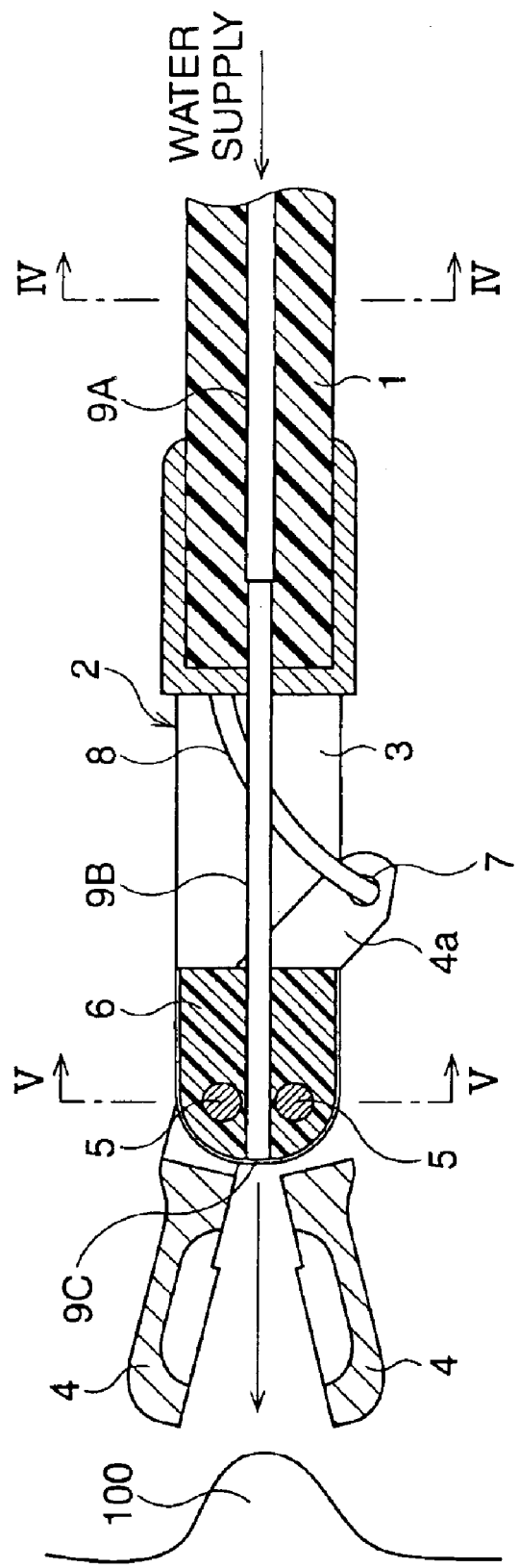
FIG. 1 is a cross-sectional elevational view of the fore-end section of a bipolar high-frequency forceps for an endoscope which is an embodiment of the present invention.

The present invention is described below with reference to the embodiments shown in the drawings.

Figure 2:
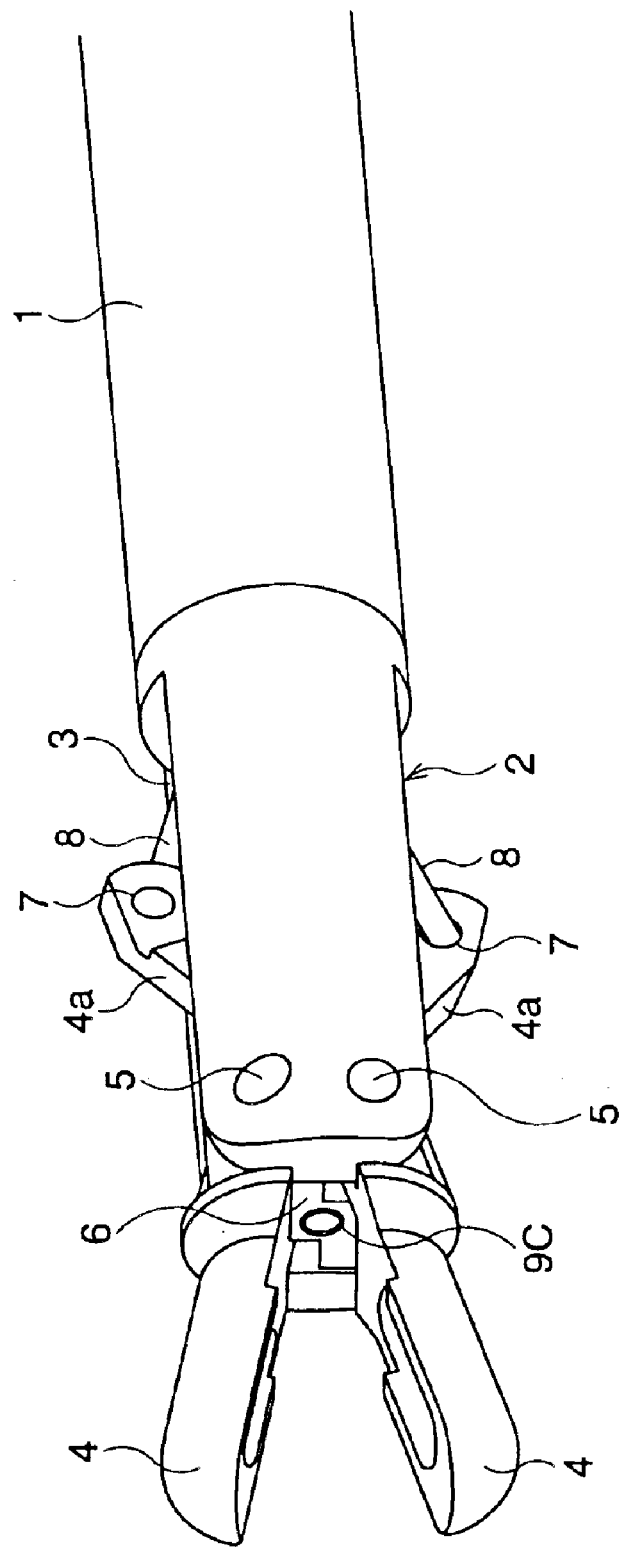
FIG. 2 is a perspective view of the bipolar high-frequency forceps in FIG. 1.
Figure 3:
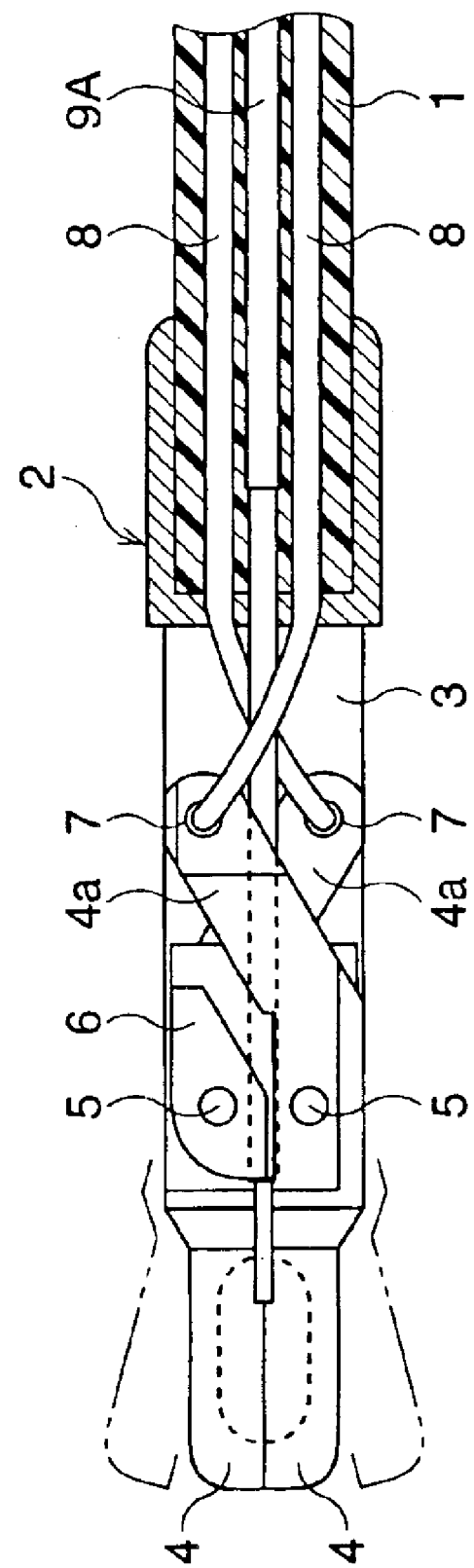
FIG. 3 is a cross-sectional elevational view of the forceps, with parts in different cross sections being depicted in one figure.

FIG. 2 is a perspective view of the fore-end section of a bipolar high-frequency forceps for an endoscope which is an embodiment of a pincerlike instrument to which the present invention is applied. In FIG. 2, a pair of the pincerlike high-frequency electrodes or limbs 4 is shown with the limbs 4 being open. FIG. 1 is a cross sectional view of the forceps in FIG. 2. FIG. 3 is a cross sectional view of the forceps with their limbs 4 closed. However, in FIG. 3, parts included in different sections are depicted in one figure in order to show the structure of the opening and closing mechanism of the limbs 4.

A flexible sheath 1 is inserted into and extracted from a treatment-instrument insertion channel of an endoscope which is not depicted. For example, the diameter of the flexible sheath 1 is about 2 to 3 mm and its length is about 1 to 2 m. Further, a multi-lumen tube having three channels, is formed of tetra fluoride ethylene resin, which has substantial electric non-conductance and flexibility, and is used for the flexible sheath 1.

Figure 4:
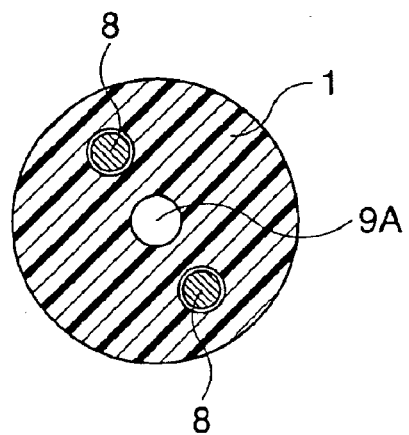
FIG. 4 is the cross sectional view of the forceps along line IV—IV of FIG. 1.

As shown in FIG. 4 that depicts the cross sectional view along line IV—IV of FIG. 1, a water supply channel 9A is formed coaxially over the length of the sheath 1. Two guide channels for the electric-conductive operating wires 8 are formed along side the water supply channel 9A over the length of the flexible sheath 1 with the water supply channel 9A in between.

As shown in FIG. 1 through FIG. 3, a fore-end member 2 made of hard plastics or ceramics, that has electric non-conductance, for example, is fixedly connected at the distal end of the flexible sheath 1. Further, a slit 3 with a certain width is formed on the fore-end member 2 with its opening facing forward.

Figure 5:
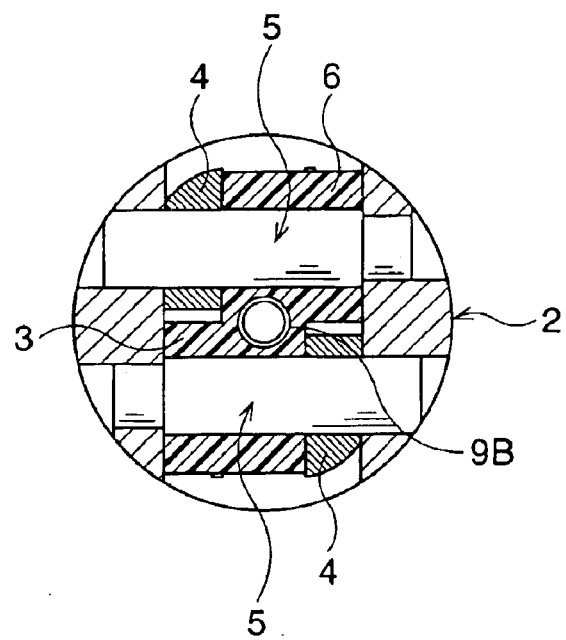
FIG. 5 is the cross sectional view of the forceps along line V—V of FIG. 1.

As is shown in FIG. 5, depicting the cross sectional view along line V—V of FIG. 1, stainless steel pivots 5 are provided on the front-end section of the fore-end member 2. The two pivots 5 are arranged in parallel with each other and perpendicularly cross the slit 3 with the center axis of the fore-end member 2 between them.

Namely, the two pincerlike high-frequency electrodes 4 which are made of conductive metallic material, such as stainless steel, are journaled onto their respective pivots 5, so that the pair of pincerlike high-frequency electrodes 4 can be made to open and close as well as the pincers.

Further, inside the front-end section of the slit 3, a non-conductive spacer 6 is disposed between both the pincerlike high-frequency electrodes 4 in order to electrically insulate the two pincerlike high-frequency electrodes 4. Namely, the two pivots 5 penetrate the non-conductance spacer 6 in the lateral direction.

Note that, in FIG. 3, the closed appearance of the pincerlike high-frequency electrodes 4 is depicted by solid lines and the open appearance is depicted by two-dot chain lines. In this embodiment, each of the pincerlike high-frequency electrodes 4 has a recessed concave portion on the inner sides of pincerlike electrodes that face and join one another when they are closed. However, the shape of pincerlike portion is not restricted to that represented in this embodiment and each of the electrodes can also be a plain limb or any other type.

Arm sections 4a are integrally formed on the rear side of each of the pincerlike high-frequency electrodes 4. Namely, the arm sections 4a extend out rearward from the pivotal portions supported by each of the pivots 5. A hole 7 is formed close to the end of each of the arm sections 4a, so that the ends of two electric-conductive operating wires 8, which are electrically insulated from each other, are separately connected to the arm sections 4a through the respective holes 7.

Namely, one of the electric-conductive operating wires 8 is electrically and mechanically connected to one of the pincerlike high-frequency electrodes 4, and the other electric-conductive operating wires 8 is electrically and mechanically connected to the other pincerlike high-frequency electrode 4. When both of the electric-conductive operating wires 8 are retracted or pushed forward, the pair of the pincerlike high-frequency electrodes 4 is opened or closed by rotating about the pivots 5.

As is shown in FIG. 1, the fore end of the water supply channel 9A, which is coaxially formed in the flexible sheath 1, is fixedly connected to the rear end of a water supply channel 9B made of a hard plastic pipe with electric non-conductance, for example, so that the fore end of the water supply channel 9A is not exposed to the open air at the distal end of the flexible sheath 1.

The water supply channel 9B is coaxially and directly aligned with the fore-end member 2 that is coaxial with the distal end of the flexible sheath 1. The water supply channel (pipe) 9B penetrates the non-conductance spacer 6 and its opening is directed strait forward to the outside from the front end face of the non-conductance spacer 6 (a water ejection opening 9C).

Namely, the water ejection opening 9C is arranged at the position between the two pincerlike high-frequency electrodes 4 that corresponds to the base section of the pair of the pincerlike high-frequency electrodes 4. Therefore, when the water is ejected from the water supply ejection opening 9C, the water jets out forward from the portion between the pincerlike high-frequency electrodes 4 that are opened.

Figure 6:
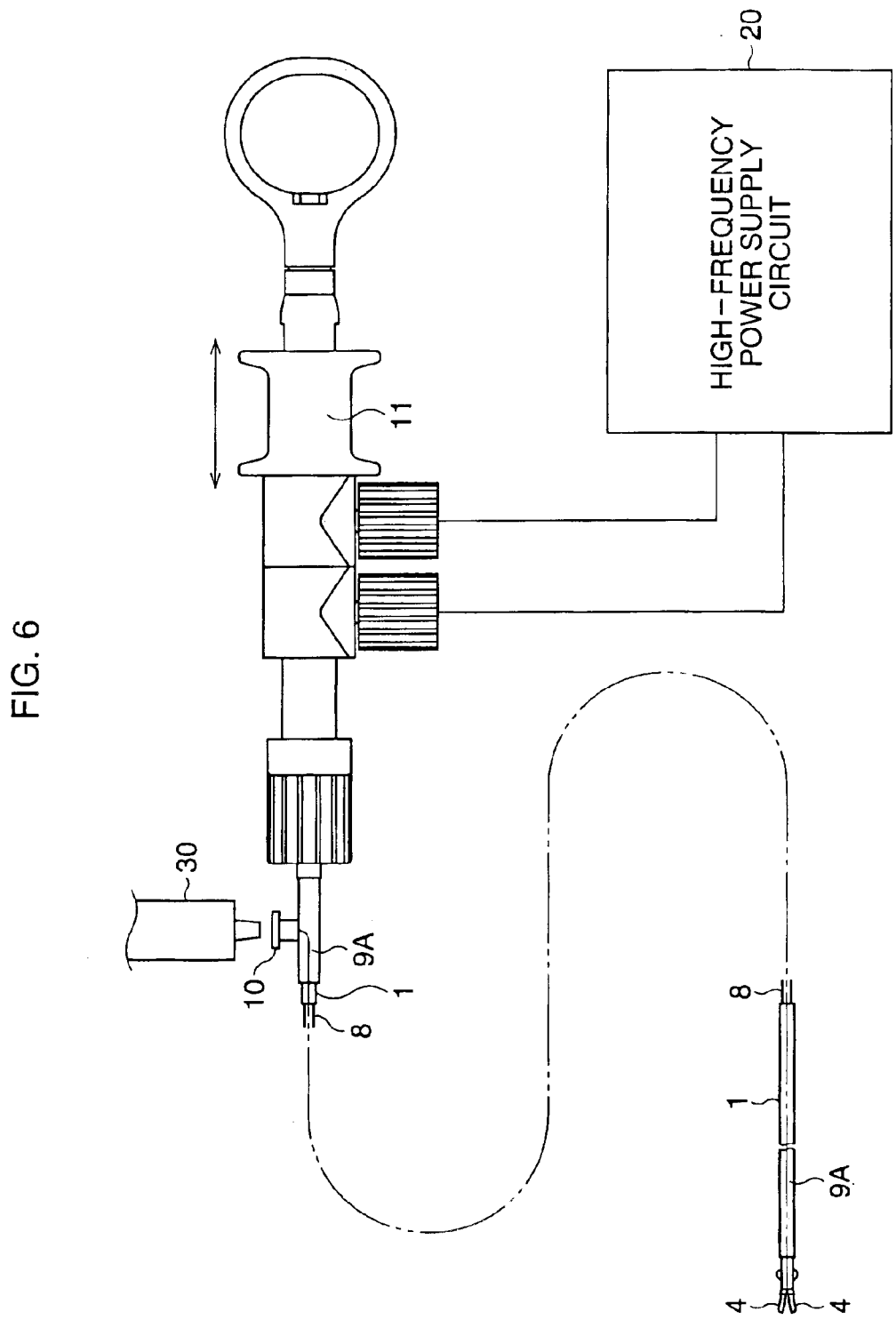
FIG. 6 schematically illustrates the general structure of the endoscope and forceps of the embodiment.

The two electric-conductive operating wires 8 are arranged inside the flexible sheath 1 along the axis and over the length of the flexible sheath 1. The two electric-conductive operating wires 8 can be moved forward and backward inside the flexible sheath 1 along the axis by operating an operational ring 11 on the operational portion that is connected at the base end of the flexible sheath 1, as shown in FIG. 6.

The base end terminals of the two electric-conductive operating wires 8 are connected to a high-frequency power supply circuit 20 at the operation portion. When the high-frequency power supply circuit 20 is turned on, a high-frequency electric current passes between the pair of pincerlike high-frequency electrodes 4.

Further, at the base end of the flexible sheath 1, a protruding water supply mouthpiece 10 that is connected to the water supply channel 9A is provided. Namely a water supply instrument 30 is connected to the protruding water supply mouthpiece 10, so that the water can be supplied into the water channel 9A and spurted out from the water supply ejection opening 9C at the front end.

As described above, according to the pincerlike instruments of the present embodiment for an endoscope, blood can be washed away from a bleeding affected part 100 by ejecting detergent water onto the affected part 100 from the water supply ejection opening 9C, provided on the base or the root portion of the pincerlike high-frequency electrodes 4, when the pair of electrodes are open, as shown in FIG. 1.

Further, when the blood is being washed away, the pair of pincerlike high-frequency electrodes 4 is already positioned at the place where the pair of the electrodes 4 can pinch the hemorrhaging part 100. Namely, the pincerlike high-frequency electrodes 4 can be closed to pinch the affected part 100 immediately after washing blood away from the affected part 100 and a high-frequency current is supplied to the electrodes 4. Thereby, the high-frequency electric current can be supplied to the affected part 100 positioned between the pair of pincerlike high-frequency electrodes 4 so that the hemostasis is achieved by cauterization of the mucous membrane at the affected part.

Note that, the invention is not restricted to the example shown in the above-described embodiment. For example, a simple flexible tube can be used as the flexible sheath 1. Further, the invention can be applied to various types of forceps or pincerlike instruments for an endoscope and is not restricted to the forceps described in this embodiment.

According to the present invention, the ejection opening, formed on the base section on which the pair of limbs that opens and closes as pincers is supported, faces forward and is disposed between the limbs. Thereby, the pair of limbs is already positioned in an open state at a position where the limbs can pinch the hemorrhaging part when the blood is being washed away by the water ejected from the ejection opening. Therefore, the affected part can be pinched by the limbs immediately after washing the blood away from the affected part so that any required treatment can be suitably carried out easily and right away.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2003-072865 (filed on Mar. 18, 2003), which is expressly incorporated herein, by reference, in its entirety.

What is claimed is:

1. A pincerlike instrument for an endoscope, comprising:
   a flexible sheath;
   a pair of limbs provided at the fore-end of said flexible sheath, that open and close as a pincers, by remote operations from the base-end of said flexible sheath;
   a water supply channel that is formed inside said flexible sheath for ejecting water from the fore-end of said flexible sheath by supplying said water from said base-end of said flexible sheath; and
   a pair of pivots such that one pivot of said pair of pivots is arranged on one side of the axis and another pivot of said pair of pivots is arranged on another side of the axis, at the front-end section of said flexible sheath,
   wherein a water ejection opening of said water supply channel is disposed at the base portion of said pair of limbs and between said two limbs, with said water ejection opening facing forward, and
   wherein each of said limbs is separately rotatable about a respective pivot of said pair of pivots, and said water supply channel passes between said pair of pivots.

2. An instrument according to claim 1, wherein said water ejection opening is positioned to be coaxial with the axis of the front-end section of said flexible sheath.

3. An instrument according to claim 1, wherein said limbs are insulated from each other and function as high-frequency current electrodes.

4. The instrument according to claim 1, further comprising:
   first and second electric-conductive operating wires each electrically and mechanically connected to a respective limb of the pair of limbs,
   wherein the water supply channel is positioned between the first and second electric-conductive operating wires over an entire length of the first and second electric-conductive operating wires.

5. The instrument according to claim 1, further comprising:

first and second arm sections each formed integrally with a respective limb of the pair of limbs and extending away from the fore-end beyond the pair of pivots, wherein the first and second arm sections are connected to a respective electric-conductive operating wire configured to mechanically rotate the pair of limbs about the pair of pivots, respectively.

6. The instrument according to claim 1, wherein the water supply channel includes a hard plastic pipe having the water ejection opening and fixedly connected to an intra-sheath portion of the water supply channel at a position inside the flexible sheath, and wherein the intra-sheath portion of the water supply channel is not exposed to an exterior of the fore-end of the flexible sheath.

7. The instrument according to claim 1, further comprising:

a non-conductive spacer disposed between the pair of limbs and electrically insulating the pair of limbs from one another, wherein the pair of pivots respectively penetrate the non-conductance spacer in a generally lateral direction.

8. The instrument according to claim 1, further comprising:

a fore-end member including at least one of hard plastic or ceramic, the fore-end member being fixedly connected to the fore-end of the flexible sheath and including a slit facing forward.

* * * * *